United States Patent
Mathai et al.

(10) Patent No.: US 8,222,567 B2
(45) Date of Patent: Jul. 17, 2012

(54) SYSTEM AND METHOD FOR LASER SHOCK PEENING

(75) Inventors: Manu Mathai, Bangalore (IN); Paul Stephen DiMascio, Greer, SC (US); Gabriel Della-Fera, Greenville, SC (US)

(73) Assignee: General Electric Company, Schenectady, NY (US)

( * ) Notice: Subject to any disclaimer, the term of this patent is extended or adjusted under 35 U.S.C. 154(b) by 317 days.

(21) Appl. No.: 12/778,371

(22) Filed: May 12, 2010

(65) Prior Publication Data

US 2011/0278271 A1    Nov. 17, 2011

(51) Int. Cl.
*B23K 26/00* (2006.01)
*B29C 65/16* (2006.01)

(52) U.S. Cl. ......... 219/121.85; 219/121.83; 219/121.84; 219/121.6; 219/121.64; 219/128; 73/589; 356/318

(58) Field of Classification Search ............. 219/121.83, 219/121.84, 121.85, 121.6, 121.64, 128; 73/589; 356/318
See application file for complete search history.

(56) References Cited

U.S. PATENT DOCUMENTS

| | | | |
|---|---|---|---|
| 5,245,473 A * | 9/1993 | Stanton et al. | 359/577 |
| 6,324,912 B1 | 12/2001 | Wooh | |
| 7,397,421 B2 | 7/2008 | Smith | |
| 2007/0138157 A1 * | 6/2007 | Dane et al. | 219/121.85 |
| 2007/0296968 A1 * | 12/2007 | Wu et al. | 356/318 |
| 2009/0084767 A1 * | 4/2009 | Deaton et al. | 219/121.83 |
| 2011/0285994 A1 * | 11/2011 | Mathai et al. | 356/318 |

* cited by examiner

*Primary Examiner* — Dao H Nguyen
(74) *Attorney, Agent, or Firm* — Dority & Manning, P.A.

(57) ABSTRACT

A system for laser shock peening includes a laser positioned to direct a laser pulse at a first side of a work piece and a coupler on a second side of the work piece. The system further includes a Doppler shift detector positioned to measure a velocity of the coupler. A method for laser shock peening includes depositing an amount of energy from a laser pulse into a first side of a work piece and transmitting a pulse having a first frequency at a second side of the work piece. The method further includes receiving a reflected pulse having a second frequency from the second side of the work piece and determining the velocity of the work piece based on the difference between the first frequency and the second frequency.

20 Claims, 2 Drawing Sheets

SYSTEM AND METHOD FOR LASER SHOCK PEENING

FIELD OF THE INVENTION

The present invention generally involves a system and method for hardening a metal using laser shock peening. In particular, the present invention provides a system and method for providing real time monitoring of the effectiveness of the laser shock peening.

BACKGROUND OF THE INVENTION

Peening is a well-known process to improve the material properties of a metal. The peening impact, usually created by mechanical means such as a hammer blow or by a blast of shot (e.g., shot peening), plastically deforms the metal surface to produce residual compressive stresses at or below the surface and tensile stresses in the interior. The compressive stresses in the metal surface improves the metal's resistance to metal fatigue and crack growth.

A laser pulse may be used in place of a hammer blow or blast of shot to provide the peening impact on the metal surface. In a typical layer shot peening system, an opaque coating such as black tape or paint is applied to metal surface to form an ablative coating. A translucent layer, usually in the form of a flow of water, on top of the ablative coating acts as a tamp. Short laser pulses focused on the target surface explode the ablative coating, and the translucent layer directs the resulting shock wave into the surface of the target material. The laser beam may then be repositioned and the process repeated to create an array of slight indents of compression and depth in the surface of the target material. The repositioning of the laser pulse is often computer or robotically controlled to precisely direct the laser pulses at specific locations on the surface of the target material. Laser shock peening typically produces a layer of residual compressive stress near the target surface that is four times deeper than that attainable from conventional shot peening treatments.

A laser shock peening system often includes sensors and circuitry to measure the amount and location of energy deposited in the target material. For example, a piezo-electric transducer attached to the target material may be used to sense the shock wave produced by the laser pulse and produce an electric current that is proportional to the shock wave. A known disadvantage of piezo-electric transducers, however, is that the shock wave produced by the laser pulse often damages the piezo-electric transducer. As a result, multiple piezo-electric transducers are required for each laser shock peening cycle, and the ability to continuously monitor the effectiveness of the laser shock peening is limited.

Another disadvantage associated with using piezo-electric transducers to monitor the effectiveness of laser shock peening is a lack of sensitivity to slight malfunctions in the laser shock peening process that reduce the effectiveness of the process. For example, studies have shown that piezo-electric transducers lack the sensitivity to reliably identify deficiencies in the translucent layer, ablative layer, or energy level of the laser pulse. Any one of these deficiencies in the system may reduce the amount of energy deposited on the surface of the target material, with a corresponding decrease in the amount and depth of compressive stress produced in the target material. As a result, piezo-electric transducers are unable to reliably identify malfunctions in the laser shock peening process.

BRIEF DESCRIPTION OF THE INVENTION

Aspects and advantages of the invention are set forth below in the following description, or may be obvious from the description, or may be learned through practice of the invention.

One embodiment of the present invention is a system for laser shock peening. The system includes a laser positioned to direct a laser pulse at a first side of a work piece and a coupler on a second side of the work piece. The system further includes a Doppler shift detector positioned to measure a velocity of the coupler.

Another embodiment of the present invention is a system for laser shock peening that includes a laser positioned to direct a laser pulse at a first side of a work piece, a coupler on a second side of the work piece, and means for amplifying a velocity of the coupler. The system further includes a Doppler shift detector positioned to measure a velocity of at least a portion of the means for amplifying the velocity of the coupler.

The present invention also includes a method for laser shock peening. The method includes depositing an amount of energy from a laser pulse into a first side of a work piece and transmitting a pulse having a first frequency at a second side of the work piece. The method further includes receiving a reflected pulse having a second frequency from the second side of the work piece and determining the velocity of the work piece based on the difference between the first frequency and the second frequency.

Those of ordinary skill in the art will better appreciate the features and aspects of such embodiments, and others, upon review of the specification.

BRIEF DESCRIPTION OF THE DRAWINGS

A full and enabling disclosure of the present invention, including the best mode thereof to one skilled in the art, is set forth more particularly in the remainder of the specification, including reference to the accompanying figures, in which.

DETAILED DESCRIPTION OF THE INVENTION

Figure 1:
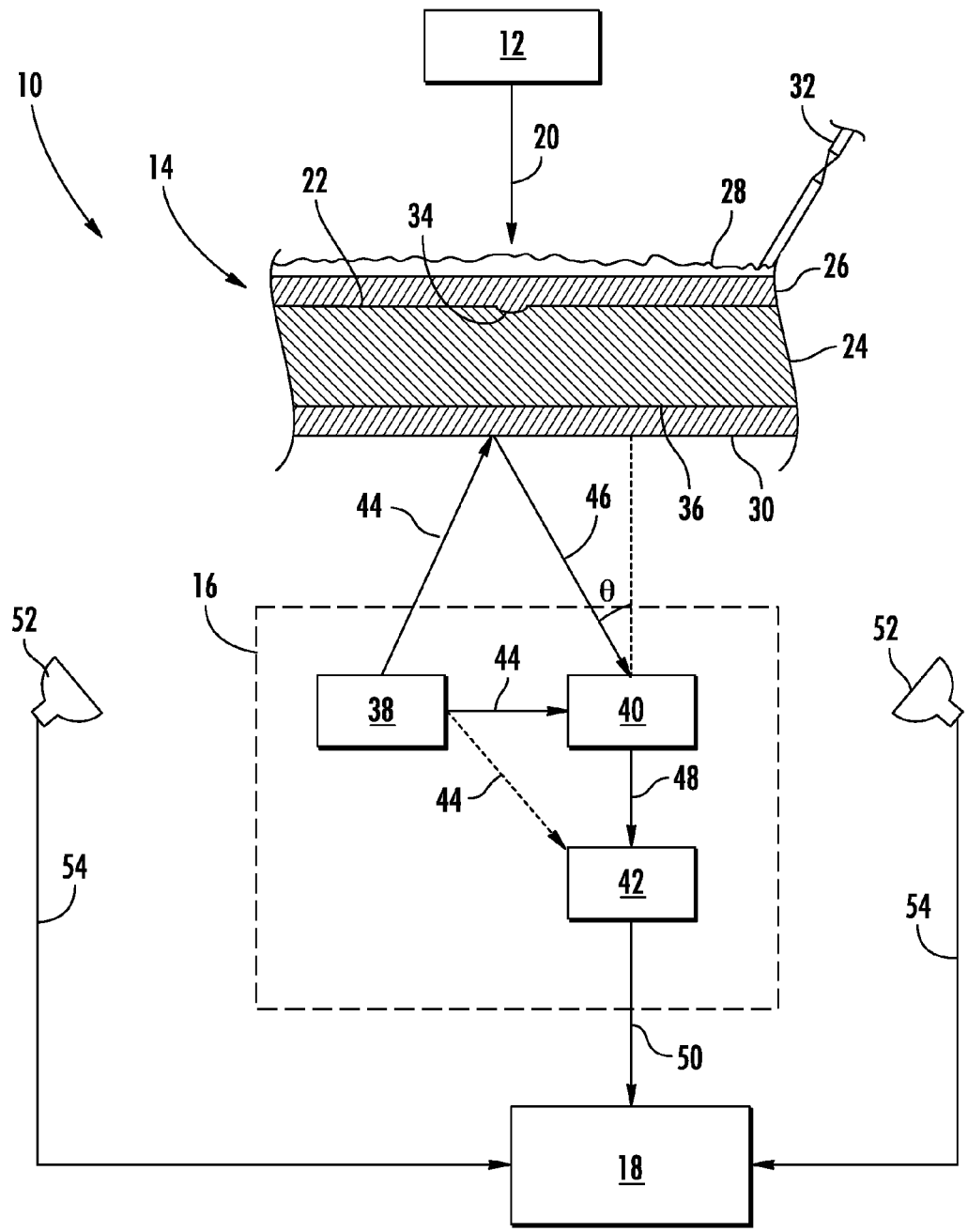
FIG. 1 shows a laser shock peening system according to one embodiment of the present invention.

Reference will now be made in detail to present embodiments of the invention, one or more examples of which are illustrated in the accompanying drawings. The detailed description uses numerical and letter designations to refer to features in the drawings. Like or similar designations in the drawings and description have been used to refer to like or similar parts of the invention.

Each example is provided by way of explanation of the invention, not limitation of the invention. In fact, it will be apparent to those skilled in the art that modifications and variations can be made in the present invention without departing from the scope or spirit thereof. For instance, features illustrated or described as part of one embodiment may be used on another embodiment to yield a still further embodiment. Thus, it is intended that the present invention covers such modifications and variations as come within the scope of the appended claims and their equivalents.

FIG. 1 shows a laser shock peening system 10 according to one embodiment of the present invention. As shown in FIG. 1, the system 10 may include a laser 12, a target 14, a Doppler shift detector 16, and a controller 18.

The laser 12 is positioned to direct a laser pulse 20 toward the target 14. The laser 12 may any laser known in the art, such as a high-energy, pulsed neodymium-glass laser, that produces the laser pulse 20 through an optical chain of mirrors and lenses. The duration, wave length, and energy level of the laser pulse 20 may be varied according to various operational considerations, such as the specific composition of the target 14, the thickness of the target 14, the number and distance between individual laser pulses 20, and the desired amount of energy to be deposited in the target 14. For example, the laser pulse 20 may be approximately 15-30 nanoseconds long, with a wave length of approximately one micron, and an energy of 50 joules or more. As a specific illustration, a 25 nanosecond laser pulse having a wave length of one micron may deposit on the order of 25 joules of energy into the target 14 and generate pressure pulses on a surface 22 of the target 14 on the order of one million pounds per square inch.

The target 14 generally includes a work piece 24 to be hardened, an ablative layer 26, a translucent layer 28, and a coupler 30. The work piece 24 may include any material that may benefit from hardening, such as aluminum alloys, titanium alloys, nickel base super alloys, cast irons, other iron alloys, and virtually any metal component having notches, holes, corners, or other features prone to fatigue failure. The ablative layer 26 may be a thin coating of opaque material applied to the surface 22 of the work piece 24. For example, the ablative layer 26 may comprise a thin layer of black tape or paint applied to the surface 22 of the work piece 24. The translucent layer 28 is typically a thin sheen of water or other semi-transparent or fully transparent material applied over the ablative layer 26. As shown in FIG. 1, for example, a water supply 32 may direct a continuous flow of water over the ablative layer 26 to form the translucent layer 28.

The combination of the translucent overlay 28 and ablative layer 26 on the surface 22 of the work piece 24 enhances the ability of the laser pulse 20 to deposit energy into the surface 22 of the work piece 24. The laser pulse 20 passes through the translucent layer 28 and strikes the ablative layer 26 where it vaporizes the ablative layer 26. Vapor produced from the ablative layer 26 absorbs the incoming laser energy, rapidly heating and expanding between the surface 22 of the work piece 24 and the translucent layer 28. The resulting pressure created between the translucent layer 28 and the surface 22 of the work piece 24 creates a shock wave that propagates through the work piece 24 to plastically deform the work piece 24 and produce a compressive stress yield 34 at the desired location in the work piece 24. The plastic deformation caused by the shock wave produces the strain hardening and compressive residual stresses in the surface 22 of the work piece 24.

The shape of the impact point on the illustrated work piece 24 is generally round, but other shapes may be used, if necessary, to provide the most efficient and effective processing conditions. The size of the area treated in one pulse depends upon a number of process specific factors, such as the composition of the work piece 24, the laser 12 being used, and other processing factors. The size of the area treated may range from approximately 2.5 millimeters to 25 millimeters in diameter, although the present invention is not limited by the size of the treated area.

The coupler 30 is generally located on a side 36 of the work piece 24 opposite the surface 22 being treated. The coupler 30 may be comprised of acoustically compliant material connected to the work piece 24 so that there is minimal transmission loss between the work piece 24 and the coupler 30. For example, the coupler 30 may be comprised of the same material as the work piece 24, or the coupler 30 may be comprised of different material with additives to tailor the density of the coupler 30 to approximate that of the work piece 24. The density of the coupler 30 may be within approximately 30 percent of the density of the work piece 24, and in particular embodiments, the density of the coupler 30 may be within approximately 20 percent or even within approximately 10 percent of the work piece 24. Similarly, the speed of sound through the coupler 30 may be within approximately 30 percent of the speed of sound through the work piece 24, and in particular embodiments, the speed of sound through the coupler 30 may be within approximately 20 percent or even within approximately 10 percent of the work piece 24. By adjusting the density, speed of sound, and acoustic impedance of the coupler 30 to approach that of the work piece 24, the shock wave produced by the laser pulse 20 propagates through both the work piece 24 and the coupler 30 at approximately the same speed, and the coupler 30 prevents or reduces the reflection of the shock wave back into the work piece 24 which could lead to propagation of preexisting cracks in the work piece 24.

A thin coating of water, oil, adhesive, glue, or other non-compressible material (not shown) may be used to attach or connect the coupler 30 to the backside 36 of the work piece 24. Propagation of the energy through the coupler 30 causes the coupler 30 to vibrate at a velocity that is proportional to the energy that propagated through and was deposited in the work piece 24. Therefore, by measuring the velocity of the coupler 30, the system 10 can determine the amount of energy deposited in the work piece 24.

The Doppler shift detector 16 may be positioned to measure the velocity of the coupler 30 based on a frequency shift, i.e., a Doppler shift, caused by the velocity of the coupler 30. The Doppler shift detector 16 may be any Doppler shift detector known in the art and may include some or all of the functional components illustrated in FIG. 1. As shown in FIG. 1, the Doppler shift detector 16 functionally includes a transmitter 38, a receiver 40, and a demodulator 42. In alternate embodiments within the scope of the invention, the transmitter 38 and receiver 40 may be combined into a single transducer component that both transmits and receives.

The transmitter 38 produces a test pulse 44 and transmits the test pulse 44 toward the work piece 24, and more specifically toward the coupler 30, and to at least one of the receiver 40 and/or the demodulator 42. The test pulse 44 may be a microwave, laser pulse, sound wave, or other similar high frequency pulse having an initial frequency $F_1$. The test pulse 44 impacts the work piece, and more specifically the coupler 30, and produces a reflected pulse 46. The relative motion of the work piece 24 and/or the coupler 30 induces a Doppler shift in the frequency of the test pulse 44, and the change in frequency between the test pulse 44 and the reflected pulse 46 may be calculated according to the following equation: $\Delta F = 2F_1(v_s/c)\cos\theta$, where $F_1$ is the initial frequency of the test pulse 44, $v_s$ is the velocity of the work piece 24 and/or the coupler 30, c is the velocity of the test pulse 44, and $\theta$ is the angle of incidence as shown in FIG. 1.

The receiver 40 may be any type of non-contact transducer that receives the test pulse 44 from the transmitter 38 and the reflected pulse 46 from the work piece 24 and/or the coupler 30 and transmits a signal 48 to the demodulator 42 that is reflective of the frequency of the test pulse 44 and reflected pulse 46. The demodulator 42 determines the velocity of the work piece 24 and/or the coupler 30 based on the Doppler shifted frequency of the reflected pulse 46 compared to the test pulse 44. The demodulator 42 then transmits a signal 50 to the controller 18 that is reflective of the calculated velocity of the work piece 24 and/or the coupler 30. Depending on the specifics of the controller 18, the demodulator 42 and/or controller 18 may include an analog-to-digital converter to convert the signal 50 to a digital value for comparison in the controller 18.

The controller 18 may comprise a comparator that receives the signal 50 from the demodulator 42 and compares the signal 50 to one or more predetermined limits programmed into the controller 18. If the signal 50 exceeds the predetermined limits, the amount of energy deposited in the work piece 24 by the laser 12 is sufficient, and the controller 18 indicates that the system 10 is functioning properly. Conversely, if the signal 50 does not exceed one or more of the predetermined limits, the amount of energy deposited in the work piece 24 by the laser 12 is not sufficient, and the controller 18 indicates that the system 10 is malfunctioning. For example, a translucent layer 28 and/or ablative layer 26 that is absent or too thin will reduce the magnitude of the shock wave produced by the laser pulse 20, producing a corresponding decrease in the amount of energy deposited in and propagated through the work piece 24. Similarly, a laser pulse 20 that is too short, incorrectly aimed, or of insufficient energy will produce a corresponding decrease in the amount of energy deposited in and propagated through the work piece 24. The decrease in energy deposited in and propagated through the work piece 24 caused by any of these possible malfunctions in the system 10 will produce a corresponding decrease in the velocity of the work piece 24 and/or the coupler 30. If this decrease in velocity of the work piece 24 and/or coupler 30 falls below one or more of the predetermined limits, the control system 18 will detect this abnormally low velocity and provide an indication that the system 10 is not operating properly. In this manner, the system 10 is able to provide real time monitoring of the effectiveness and efficiency of the laser shock peening process.

As a quantitative example of the operation of the system 10, assume that a laser pulse that deposits 25 joules of energy into a stainless steel work piece having a mass of 50 kilograms induces a vibration of 20 feet per second in an acoustically matched coupler. If it is desired to deposit at least 25 joules of energy into the work piece for each laser pulse, the controller may be programmed with predetermined limits to identify a velocity of the coupler that falls below 20 feet per second. Of course, the preceding values for energy deposited in the work piece and resulting velocity of the coupler are for illustration and example only. The actual values for these and other measurements will depend on the specific laser, work piece, geometries, and other variables associated with the shock peening system and may be readily calculated or determined by one of ordinary skill in the art.

As shown in FIG. 1, the system 10 may further include a plurality of receivers, transducers, or microphones 52 at different locations. Each microphone 52 is positioned to receive the reflection of energy waves, for example sound waves, generated by the impact of the laser pulse 20 on the surface 22 of the work piece 24 and to transmit a timing signal 54 to the controller 18. The controller 18 may then compare the timing signal 54 from each microphone 52 to triangulate the exact location of the laser pulse 20 on the surface 22 of the work piece 24. In this manner, the controller 18 can accurately map the location of each laser pulse 20 on the surface 22 of the work piece 24. In the event that the controller 18 detects a malfunction in the system 10 for any of the laser pulses 20, the controller 18 may provide the exact location of the deficient laser pulse 20 so that it may be performed again, if desired.

Figure 2:
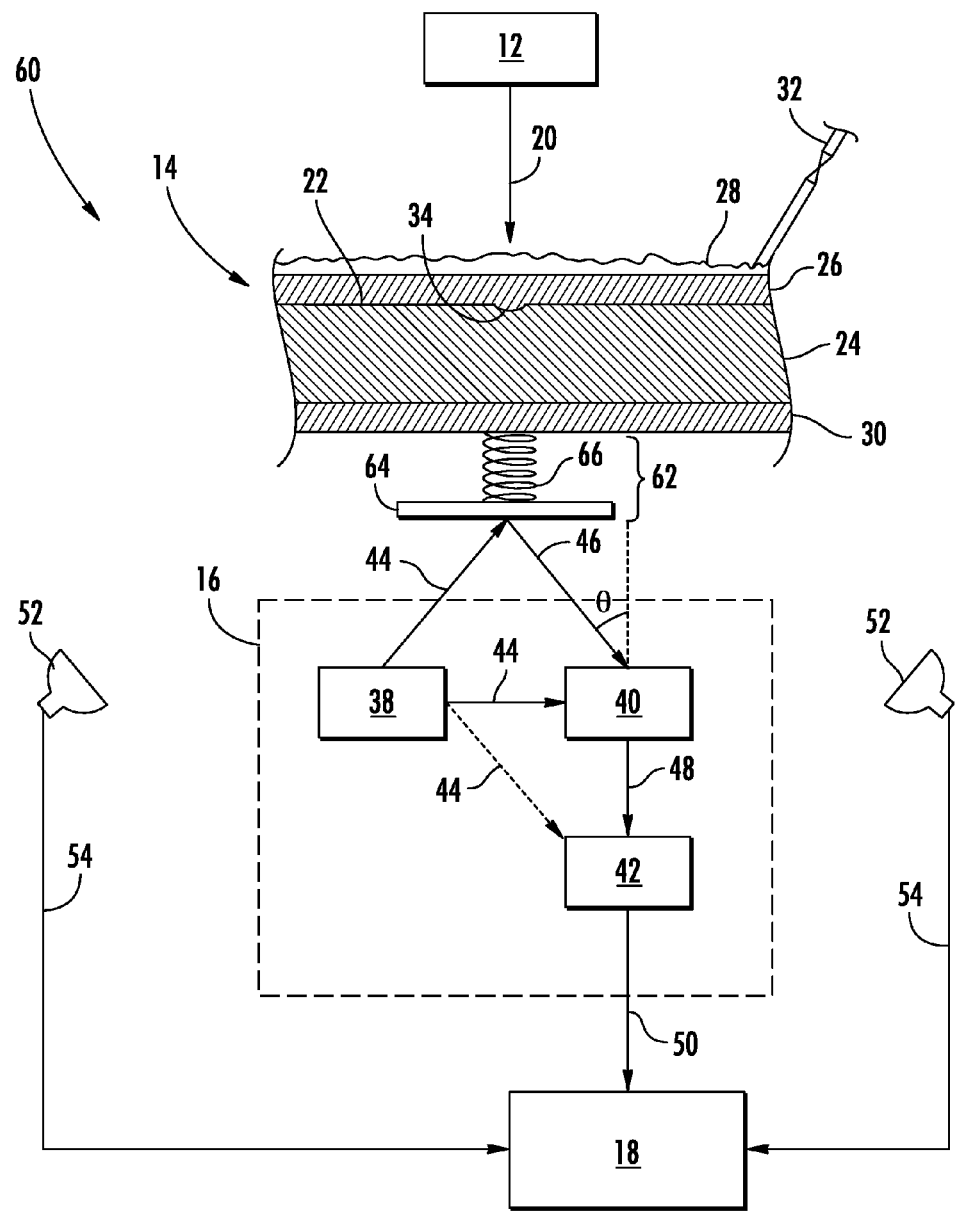
FIG. 2 shows a laser shock peening system according to an alternate embodiment of the present invention.

FIG. 2 shows a laser shock peening system 60 according to an alternate embodiment of the present invention. The system 60 again generally includes a laser 12, a target 14, a Doppler shift detector 16, and a controller 18 as previously described with respected to the embodiment illustrated in FIG. 1. The laser pulse 20 from the laser 12 passes through the translucent layer 28 and strikes the ablative layer 26 where it immediately vaporizes the ablative layer 26. Vapor produced from the ablative layer 26 absorbs the incoming laser energy, rapidly heating and expanding between the surface 22 of the work piece 24 and the translucent layer 28. The resulting pressure created between the translucent layer 28 and the surface 22 of the work piece 24 creates a shock wave that propagates through the work piece 24 to plastically deform the work piece 24 and produce the compressive stress yield 34 at the desired location in the work piece 24. The plastic deformation caused by the shock wave produces the strain hardening and compressive residual stresses in the surface 22 of the work piece 24.

The shock wave produced by the laser pulse 20 propagates through both the work piece 24 and the coupler 30 at approximately the same speed without being reflected back into the work piece 24 which could lead to propagation of preexisting cracks. Propagation of the energy through the work piece 24 causes the coupler 30 to vibrate at a velocity that is proportional to the energy that propagated through and was deposited in the work piece 24.

The system 60 shown in FIG. 2 further includes an amplifying means 62 attached to or connected to at least one of the work piece 24 or the coupler 30. The amplifying means 62 may comprise any spring mass system or accelerometer that can vibrate in response to movement of the work piece 24 and/or coupler 30. For example, as shown in FIG. 2, the amplifying means 62 may include a member 64 attached to the coupler 30 by a spring 66, band, or other material known in the art for connecting objects together. At least a portion of the amplifying means 62, such as the member 64, will vibrate at a frequency that is proportional to the square root of the stiffness of the spring 66 divided by the mass of the member 64. The mass of the member 64 and stiffness of the spring 66 may thus be selected to enhance the amplification of the velocity of the coupler 30.

The Doppler shift detector 16 functions as previously described with respect to the embodiment shown in FIG. 1, except that the test pulse 44 reflects off a portion of the amplifying means 62, such as the member 64. As a result, the relative motion of the portion of the amplifying means 62 induces a Doppler shift in the initial frequency of the test pulse 44, and the change in frequency between the test pulse 44 and the reflected pulse 46 may be calculated according to the following equation: $\Delta F = 2F_1(v_s/c)\cos\theta$, where $F_1$ is the initial frequency of the test pulse 44, $v_s$ is the velocity of the member 64, c is the velocity of the test pulse 44, and $\theta$ is the angle of incidence as shown in FIG. 2.

The Doppler shift detector 16 determines the velocity of the portion of the amplifying means 62 based on the Doppler shifted frequency of the reflected pulse 46 compared to the test pulse 44 and transmits the signal 50 to the controller 18 that is reflective of the calculated velocity of the portion of the amplifying means 62. The controller 18 then compares the signal 50 to one or more predetermined limits programmed into the controller 18 to determine if the system 60 is operating within normal parameters, as previously described.

The embodiments described and illustrated in FIGS. 1 and 2 may provide a method for real-time monitoring the effectiveness and efficiency of laser shock peening. As previously described, the method includes depositing an amount of energy from the laser pulse 20 into the surface 22 or first side of the work piece 24. The energy deposited in the work piece 24 by the laser pulse 20 causes the work piece 24, coupler 30, and/or amplification means 62 to move at a velocity that is reflective of the amount of energy deposited in the work piece 24.

The method further includes transmitting the test pulse 44 having a first frequency $F_1$ at the second side 36 of the work piece 24, coupler 30, and/or the amplification means 62 and receiving the reflected pulse 46 having a second frequency. The method determines the velocity of the work piece 24, coupler 30, and/or amplification means 62 based on the difference between the first frequency and the second frequency. The method may then compare the velocity of the work piece 24, coupler 30, and/or amplification means 62 to one or more predetermined limits to determine the efficiency and/or effectiveness of the laser shock peening. The method may further include receiving a reflection of energy waves from the laser pulse 20 and determining the position of the energy deposited in the work piece 24 based on the energy waves from the laser pulse 20.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they include structural elements that do not differ from the literal language of the claims, or if they include equivalent structural elements with insubstantial differences from the literal languages of the claims.

What is claimed is:

1. A system for laser shock peening, comprising:
   a. a laser positioned to direct a laser pulse at a first side of a work piece;
   b. a coupler on a second side of the work piece; and
   c. a Doppler shift detector positioned to measure a velocity of said coupler.

2. The system for laser shock peening as in claim 1, wherein said coupler has a coupler density and the work piece has a work piece density and said coupler density is within approximately 30 percent of the work piece density.

3. The system for laser shock peening as in claim 2, wherein said coupler density is within approximately 10 percent of the work piece density.

4. The system for laser shock peening as in claim 1, wherein said Doppler shift detector transmits a signal that is reflective of said velocity of said coupler.

5. The system for laser shock peening as in claim 4, further including a controller that receives said signal.

6. The system for laser shock peening as in claim 5, wherein said controller includes at least one predetermined limit.

7. The system for laser shock peening as in claim 1, further including a plurality of transducers positioned to receive a reflection of energy waves.

8. The system for laser shock peening as in claim 7, wherein each of said plurality of transducers transmits a timing signal.

9. The system for laser shock peening as in claim 8, further including a controller that receives said timing signal from each of said plurality of transducers.

10. A system for laser shock peening, comprising:
    a. a laser positioned to direct a laser pulse at a first side of a work piece;
    b. a coupler on a second side of the work piece;
    c. means for amplifying a velocity of said coupler; and
    d. a Doppler shift detector positioned to measure a velocity of at least a portion of said means for amplifying said velocity of said coupler.

11. The system for laser shock peening as in claim 10, wherein said Doppler shift detector transmits a signal that is reflective of said velocity of at least a portion of said means for amplifying said velocity of said coupler.

12. The system for laser shock peening as in claim 11, further including a controller that receives said signal.

13. The system for laser shock peening as in claim 12, wherein said controller includes at least one predetermined limit.

14. The system for laser shock peening as in claim 10, further including a plurality of transducers positioned to receive a reflection of energy waves.

15. The system for laser shock peening as in claim 14, wherein each of said plurality of transducers transmits a timing signal.

16. A method for laser shock peening, comprising:
    a. depositing an amount of energy from a laser pulse into a first side of a work piece;
    b. transmitting a pulse having a first frequency at a second side of the work piece;
    c. receiving a reflected pulse having a second frequency from the second side of the work piece; and
    d. determining a velocity of the work piece based on a difference between said first frequency and said second frequency.

17. The method of claim 16, further including determining said amount of energy deposited by said laser pulse into the first side of the work piece based on said velocity of the work piece.

18. The method of claim 16, further including comparing said velocity of the work piece to a predetermined value.

19. The method of claim 16, further including receiving a reflection of energy waves from said laser pulse.

20. The method of claim 19, further including determining a position of said energy deposited in the first side of the work piece based on said energy waves from said laser pulse.

* * * * *